United States Patent [19]
Kraus et al.

[11] Patent Number: 5,820,755
[45] Date of Patent: Oct. 13, 1998

[54] LEUKOCYTE FILTER UNIT

[75] Inventors: Menachem Kraus, Yavne; Jacob Yonath, Rehovot, both of Israel

[73] Assignee: Travenol Laboratories (Israel) Ltd., Ashdod, Israel

[21] Appl. No.: 936,283

[22] Filed: Sep. 24, 1997

Related U.S. Application Data

[62] Division of Ser. No. 512,446, filed as PCT/US94/01413 Feb. 8, 1994, Pat. No. 5,707,526.

[51] Int. Cl.⁶ .......................... B01D 29/00; B01D 39/00; B01D 71/00
[52] U.S. Cl. .......................... 210/483; 210/488; 210/490; 210/500.21; 210/500.29; 210/504; 210/506; 210/508
[58] Field of Search ...................... 210/483, 488, 210/489, 490, 500.21, 500.29, 504, 506, 508

[56] References Cited

U.S. PATENT DOCUMENTS

| | | | |
|---|---|---|---|
| 3,628,669 | 12/1971 | McKinnis et al. | |
| 3,874,907 | 4/1975 | Gardon et al. | |
| 3,909,383 | 9/1975 | Sato | 210/500 |
| 4,214,020 | 7/1980 | Ward et al. | 210/490 |
| 4,252,653 | 2/1981 | Beck et al. | 210/446 |
| 4,305,823 | 12/1981 | Batzer et al. | 210/654 |
| 4,330,410 | 5/1982 | Takenaka et al. | 210/767 |
| 4,446,136 | 5/1984 | Maeda et al. | 514/21 |
| 4,693,834 | 9/1987 | Hossom | 210/767 |
| 4,734,192 | 3/1988 | Champion et al. | 210/335 |
| 4,746,473 | 5/1988 | Kohn | 210/500.29 |
| 4,923,620 | 5/1990 | Pall | 210/767 |
| 4,925,572 | 5/1990 | Pall | 210/767 |
| 4,936,998 | 6/1990 | Nishimura et al. | 210/638 |
| 5,035,801 | 7/1991 | Schmer | 210/490 |
| 5,064,541 | 11/1991 | Jeng et al. | 210/767 |
| 5,137,633 | 8/1992 | Wang | 210/490 |
| 5,139,031 | 8/1992 | Guirguis | 128/771 |
| 5,164,087 | 11/1992 | Naoi et al. | 210/496 |
| 5,185,127 | 2/1993 | Vonk | 422/56 |
| 5,589,399 | 12/1996 | Allen et al. | 436/177 |

FOREIGN PATENT DOCUMENTS

| | | |
|---|---|---|
| 155003 | 9/1985 | European Pat. Off. |
| 406485 | 1/1991 | European Pat. Off. |
| 408462 | 1/1991 | European Pat. Off. |
| 89/02304 | 3/1989 | WIPO |

*Primary Examiner*—John Kim
*Attorney, Agent, or Firm*—Ladas & Parry

[57] ABSTRACT

A method for removing leukocytes from a leukocyte-containing suspension comprising passing said suspension through a filter including a nitrocellulose membrane having a pore size of 5–15 $\mu$m.

8 Claims, No Drawings

LEUKOCYTE FILTER UNIT

This is a division of application 08/512,446 filed Aug. 8, 1995, now U.S. Pat. No. 5,707,526, which is a continuation-in-part of PCT/US94/01413 filed Feb. 8, 1994.

The present invention relates to a method for removing leukocytes from suspensions containing them and especially from blood-derived suspensions. The invention also relates to a filter unit which can be used in the above method.

In recent years it has become apparent that leukocytes in transfused blood are in most cases not only superfluous but often detrimental. Leukocytes in the blood have been found to cause non-hemolytic febrile reactions and alloimmunization as well as to harbor viruses.

Donated blood can be used without prior treatment ("whole blood"), or, more frequently, processed to produce a red cell or platelet concentrate. Various methods have been developed to remove leukocytes from these blood products, the most popular being filtration methods.

EP 155003 (to Asahi) and U.S. Pat. No. 4,925,572 (to Pall) describe filtration methods using fibrous, non-woven media to capture the leukocytes as the blood suspension is passed through them. A leukocyte removal rate of over 98% can be obtained using these methods. The disadvantage of these methods is that the filter units used in them have to be composed of many layers of filter media in order to reduce leukocyte counts efficiently while at the same time providing a reasonable flow rate. This makes industrial assembly cumbersome and expensive.

An alternate method of leukocyte filtration has been described in Patent Application EP 406485 (to NPBI Nederlands). This method uses continuous porous membranes for the filtration process instead of fibers. One of the materials used for preparing the membranes described in the above application was cellulose acetate, which was found to give the best results. However, as can be seen in FIG. 9 of the above application, over 35% of the leukocytes remained in the blood filtrate, resulting in a leukocyte removal of less than 65% as compared to greater than 98% for conventional methods. The authors of the above application came to the conclusion that a series of stacked membranes having decreasing pore size in the blood flow direction ('asymmetric filter') showed a larger leukocyte removal capacity than membranes of uniform pore size. However, only a 25% leukocyte removal percentage was obtained with this 'asymmetric' filter, which contained a series of 8 membranes (FIG. 8). The filtration method described in the above application is therefore not useful for the purpose of leukocyte removal from blood products.

Other recent patents have described the use of polyvinylidene fluoride and polyvinyl formal membranes for use in leukocyte removal (see e.g. WO 89/02304).

It is an object of the present invention to provide a method for removing leukocytes from a blood-derived suspension which is efficient, simple and inexpensive.

It is a further object of the invention to provide a filter unit for use in such a method.

In accordance with this invention there is thus provided a method for removing leukocytes from a leukocyte-containing suspension comprising passing the suspension through a filter including a nitrocellulose membrane having a pore size of 5–15 $\mu$m.

It has surprisingly been found that by using commercially available nitrocellulose membranes, it has been possible to obtain a leukocyte removal percentage of between 97–99% using no more than 2 layers (Note: in this application, a membrane is defined as a continuous, nonfibrous porous matrix, and a layer is defined as consisting of one or more identical filtering elements). This result is unexpected since nitrocellulose membranes are known to be strong binding matrices for proteins. Due to this property they are used extensively in diagnostic kits where protein probes (antigens or antibodies) are irreversibly bound to the membrane surface. It could have been expected that such membranes would clog very easily upon contact with blood due to the binding of blood proteins and corpuscles. It was therefore surprising to find that such membranes are very efficient leukofilters. The filtration is accomplished with a minimal loss of erythrocytes, and blood flow is equivalent to that of conventional fiber filters.

Without limiting the invention in any way, it is thought that the mechanism by which this separation works is probably related to a selective adsorption of leukocytes on the membrane surface. The separation cannot depend on size alone, as erythrocytes and many leukocyte types are of similar size. The invention, however, does not depend on any particular theory of separation.

The method of the invention can be carried out using a single nitrocellulose membrane. Alternatively, two nitrocellulose membranes can be used, or a non-woven or membrane prefilter overlying a nitrocellulose membrane. In a further embodiment of the invention, non-woven fiber sheets can be inserted between individual nitrocellulose membranes so as to act as spacers. Ordinarily, no more than two layers are necessary in order to obtain optimal results. The non-woven prefilter can be prepared from polymer fibers such as polyesters, polyurethane and polypropylene.

The pore size of commercial nitrocellulose membranes compatible with the method of the invention ranges from 5–15 $\mu$m, preferably 8–12 $\mu$m, and more preferably 8–10 $\mu$m. Nitrocellulose membranes with pore sizes greater than 15 $\mu$m are generally not available commercially. However, if such membranes become available, it may also be possible to use them in the invention. The pore size of the prefilter also ranges from 5–15 $\mu$m.

Nitrocellulose membranes which have been chemically modified may also be used in the method of the invention. This chemical modification may be accomplished by performing a surface grafting reaction in which the membrane is exposed to a suitable initiator while in contact with a monomer. The initiator may be chemical, or it may be gamma or U.V. radiation. Suitable monomers can be various acrylic monomers carrying functional groups such as hydroxy, carboxy or others.

In accordance with this invention there is also provided a filter unit having a filter for removing leukocytes from a leukocyte-containing suspension, the filter including a nitrocellulose membrane having a pore size of 5–15 $\mu$m.

Such a filter unit can be constructed, for example, from a conventional reusable filter holder. One or two layers according to the invention are placed in the filter holder which is tightly closed and connected to a reservoir containing a unit of blood or blood product. The blood or blood product is then forced through the filter unit by applying hydrostatic pressure. The layers can be easily replaced after one or more blood units have been filtered through them. Alternatively, the filter unit can be constructed from a disposable filter housing into which the layers are heat sealed, glued or clamped mechanically.

Various leukocyte-containing suspensions can be filtered using the method of the invention. These include whole blood, packed red blood cells and platelet concentrate.

The following examples come to further illustrate and describe the invention disclosed herein. The invention is not to be limited in scope by reason of any of the following examples.

EXAMPLE 1

A 25 mm diameter nitrocellulose membrane having a nominal pore size of 12 µm was mounted in a holder of polysulfone. Both membrane and holder are products of Schleicher and Shuell, Germany. Whole blood that was stored for 7 days at 5° C. with citrate anticoagulant was filtered through the filter unit at a hydrostatic pressure of 0.08 atm. The effective filtration area was 3.2 cm$^2$ and the flow rate was 0.53 mL/min.

Results: When the number of cells in the filtrate was measured, the leukocyte count was found to be reduced from 5600 cells per µl in the original blood to 200 cells per µL, a reduction of 96.5%, while the erythrocyte count remained practically unchanged ($4.7 \times 10^6$ to $4.6 \times 10^6$ cells/µl).

EXAMPLE 2

The procedure of Example 1 was repeated, except that an additional nitrocellulose membrane having a nominal pore size of 8 µm was added beneath the first membrane. The filtration rate was 0.4 mL/min.

Results: The filtered blood was found to contain 50 leukocytes/mL (a 99.1% reduction) and $4.6 \times 10^6$ erythrocytes/mL.

EXAMPLE 3

The procedure of Example 2 was repeated, except that the two layers were a 8 µm nitrocellulose membrane overlayed with a 5 µm polyvinyl-chloride prefilter. 24 hrs.-old blood was filtered at a rate of 0.5 mL/min.

Results: The leukocyte count of the filtered blood dropped from 10,100 cells/µl to 100 cells/µl (a 99% reduction) while the erythrocyte count slightly dropped from $3.9 \times 10^6$ to $3.8 \times 10^6$ cells/µl.

EXAMPLE 4

The procedure of Example 3 was repeated, except that the 8 µm nitrocellulose membrane was replaced with a 12 µm membrane, and a red cell concentrate was used instead of whole blood. The red cell concentrate was 7 days old and stored at 5° C. The filtration rate was 2.0 mL/min.

Results: The leukocyte count dropped 97.3% from 7300 to 200 leukocytes/µl while the erythrocyte count dropped slightly from $8.3 \times 10^6$ to $7.9 \times 10^6$ cells/µl.

EXAMPLE 5

The procedure of Example 3 was repeated, except that a non-woven polyurethane prefilter was placed on top of a 12 µm nitrocellulose membrane. A membrane holder made of Delrin (Gelman Scientific, U.S.A.) was used having an effective filtration area of 3.7 cm$^2$. 48 hrs.-old whole blood was filtered at a rate of 2.1 mL/min.

Results: The leukocyte count was reduced from 7000 to 100 cells/µl (a 98.6% reduction) while the erythrocyte count remained substantially the same ($4.0 \times 10^6$ to $3.9 \times 10^6$ cells/µl).

EXAMPLE 6

The procedure of Example 1 was repeated, except that a 8 µm nitrocellulose membrane grafted with hydroxy-ethyl-metacrylate was used. The blood flow rate was 0.5 mL/min.

Results: The filtrate contained 50 leukocytes per µl (a 99.1% reduction) while the erythrocyte count remained almost unchanged ($4.5 \times 10^6$, down from $4.6 \times 10^6$).

EXAMPLE 7

Three 47 mm diameter nitrocellulose membranes of 12 µm pore size were mounted in a polycarbonate holder resulting in a 12 cm$^2$ effective filtration area. The membranes were overlayed with a prefilter comprising four identical sheets of polyester fiber. A unit (290 ml) of packed red blood cells (PRC) containing citrate-phosphate-dextrose (C.P.D.) anticoagulant was prepared by adding 100 ml of SAG-M preservation solution to a final hematocrit of 60%. The filtration was performed at room temperature 6 hrs. after donation.

Results: The first 50 ml of PRC were filtered in 10 min. The leukocyte count of the filtered PRC was found to have dropped from 7400 cells/µL to 4 cells/µL.

EXAMPLE 8

The procedure of Example 7 was repeated, except that a 20 hrs.-old PRC unit was used. The prefilter comprised 8 identical sheets of non-woven polyester, each sheet having a thickness of approximately 0.5 mm and a fiber diameter of 5–8 µm. The first 70 ml were filtered in 15 min.

Results: The leukocyte count was found to be reduced from 13100 cells/µL to 16 cells/µL. No significant changes were observed in the hematocrit (49.4% vs. 50.5%) or hemoglobin concentration (17.0 gr% vs. 17.7 gr%) after filtration.

EXAMPLE 9

The procedure of Example 8 was used with 6 hrs.-old PRC which had been stored at 20°–22° C., and was found to have a 49% hematocrit after addition of SAG-M. The rate of filtration was 152 ml/20 min.

Results: The leukocyte count dropped from 5500 cells/µL to 30 cells/µL, while the hematocrit remained at 48–48.6%.

EXAMPLE 10

The procedure of Example 8 was repeated with 7 days old PRC having a 62.1% hematocrit and 21.9 gr% hemoglobin concentration. 36 ml were filtered in 20 min.

Results: The Leukocyte count was reduced from 4500 cells/µL to about 2 cells/µL. The post-filtration hematocrit was 60.3–61.3% and the hemoglobin concentration was 21.0–21.1 gr%.

EXAMPLE 11

In this Example, the filter comprised a prefilter composed of 5 identical sheets of non-woven fiber as in Example 8, and 3 nitrocellulose membranes as in Example 7 interspersed by 3 spacer sheets of the same non-woven fiber as in the prefilter. All other parameters were as in Example 8.

Results: A 6% improvement in the flowrate was achieved without affecting the parameters of the filtered PRC. When the filter was used in the procedure of Example 9, a 19% improvement in the flowrate was obtained.

EXAMPLE 12

The procedure of Example 11 was repeated in a larger diameter system having an effective filtration area of 50 cm$^2$. 360 ml of PRC treated as in Example 7 were filtered in less than 10 min. The pre-filtration values of the PRC were: leukocyte count—8300 cells/µL; hematocrit—47.9%; hemoglobin—17.2 gr%; red blood cell count—$5.99 \times 10^6$ cells/µL.

Results: The post-filtration values of the PRC were respectively: 3 cells/μL; 47.2–48%; 17.0–17.1 gr%; 5.90–5.93×10$^6$ cells/μL.

EXAMPLE 13

The configuration of Example 1 was used with a platelet concentrate containing 1.1×10$^6$ plt/μL and 800 leukocytes/μL. The filtration rate was 4 ml/2.5 min. After the nitrocellulose membrane surface was modified, e.g. by coating it with a polymer containing hydroxyl and sulfonic groups, the flowrate was increased to 4 ml/1.8 min.

Results: The leukocyte count was reduced to 200 cells/μL and the platelet count ranged between 0.34–1.04×10$^6$.

EXAMPLE 14

A filter unit having 43 cm$^2$ effective filtration area was used to filter a whole blood unit, containing C.P.D. anti-coagulant, 6 hrs after donation. The filter consisted of one layer of 8μ nitrocellulose membrane, two layers of 12μ nitrocellulose membrane, and 22 layers of prefilter material, made of non-woven polyester fibers 5–7μ in diameter.

Two spacer sheets of the same non-woven material were used to separate between the membranes.

The whole unit was sealed inside a plastic holder, and was sterilized by Γ-irradiation.

460 ml of whole blood were filtered under 90 cm pressure-head in 13 min. The leukocyte count was reduced by filtration from 7300/μl to 7/μl, while the R.B.C. (Red Blood Cells) count remained unchanged (4.18×106/μl vs 4.12×106/μl).

EXAMPLE 15

20 hrs old C.P.D.-anti-coagulated blood was used in this example.

The blood was stored at 22° C. before filtration. The filter unit was the same as in Example 14, except that three layers of 12μ nitrocellulose membrane were used, and sterilization was made by autoclave at 121° C.

485 ml of whole blood were filtered in 10 min. Leukocytes were reduced by filtration from 6700/μl to 8/μl. RBC count remained unchanged: 4.88×106/μl vs 4.92×106/μl.

We claim:

1. A filter unit for a blood-derived suspension containing both leukocytes and erythrocytes, said unit having a filter for removing leukocytes from said suspension, said filter including a plurality of layers all capable of passing erythrocytes, at least two of said layers being nitrocellulose membranes, wherein said nitrocellulose membranes include at least one nitrocellulose membrane having a pore size of 5–15 microns blocking said leukocytes while passing said erythrocytes and at least two of said layers being non-woven fibrous media.

2. A filter unit according to claim 1, and wherein at least one of said plurality of layers comprises a non-woven polymer fiber which constitutes a pre-filter.

3. A filter unit according to claim 2, and wherein one of said plurality of layers includes a plurality of nitrocellulose membranes interspersed by non-woven polymer fiber spacers.

4. A filter unit according to claim 3, wherein said nitrocellulose membranes includes a nitrocellulous membrane which is chemically modified by a surface grafting reaction while in contact with a monomer.

5. A filter unit according to claim 2, wherein said nitrocellulose membranes includes a nitrocellulous membrane which is chemically modified by a surface grafting reaction while in contact with a monomer.

6. A filter unit according to claim 1, and wherein one of said plurality of layers includes a plurality of nitrocellulose membranes interspersed by non-woven polymer fiber spacers.

7. A filter unit according to claim 6, wherein said nitrocellulose membranes includes a nitrocellulous membrane which is chemically modified by a surface grafting reaction while in contact with a monomer.

8. A filter unit according to claim 1, wherein said nitrocellulose membranes includes a nitrocellulous membrane which is chemically modified by a surface grafting reaction while in contact with a monomer.

* * * * *

UNITED STATES PATENT AND TRADEMARK OFFICE
CERTIFICATE OF CORRECTION

PATENT NO. : 5,820,755
DATED      : October 13, 1998
INVENTOR(S) : MENACHEM KRAUS, et al.

It is certified that error appears in the above-indentified patent and that said Letters Patent is hereby corrected as shown below:

On title page, item [62], "filed as" should be --which is a CIP of--.

On title page, insert --[30] foreign application priority data date February 9, 1993 [IL] Isreal 104,670--.

On the title page, item [56], before "12/1996" insert --5,589,399--

Signed and Sealed this

Eighth Day of June, 1999

Attest:

Q. TODD DICKINSON

*Attesting Officer*      *Acting Commissioner of Patents and Trademarks*